US012082793B2

(12) United States Patent
Wong et al.

(10) Patent No.: US 12,082,793 B2
(45) Date of Patent: Sep. 10, 2024

(54) SYSTEMS AND METHODS OF STEERABLE ELONGATE DEVICE

(71) Applicant: INTUITIVE SURGICAL OPERATIONS, INC., Sunnyvale, CA (US)

(72) Inventors: Serena H. Wong, Los Altos, CA (US); Benjamin G. Cohn, Oakhurst, CA (US); Hans F. Valencia, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/328,606

(22) Filed: Jun. 2, 2023

(65) Prior Publication Data
US 2023/0309976 A1   Oct. 5, 2023

Related U.S. Application Data

(63) Continuation of application No. 16/523,910, filed on Jul. 26, 2019, now abandoned.
(Continued)

(51) Int. Cl.
*A61B 17/00* (2006.01)
*A61B 17/34* (2006.01)
(Continued)

(52) U.S. Cl.
CPC .... *A61B 17/00234* (2013.01); *A61B 17/3478* (2013.01); *A61B 34/35* (2016.02);
(Continued)

(58) Field of Classification Search
CPC .......... A61B 17/00234; A61B 17/3478; A61B 2017/00115; A61B 2017/3454;
(Continued)

(56) References Cited

U.S. PATENT DOCUMENTS 5,380,732 A   1/1995  Blade
5,389,187 A   2/1995  Marks et al.
(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Julian W Woo
*Assistant Examiner* — Bridget E. Rabaglia
(74) *Attorney, Agent, or Firm* — Haynes & Boone, LLP

(57) ABSTRACT

A method comprises deploying a tool to a passageway exit site through a lumen of a flexible elongate device. The flexible elongate device comprises a proximal end, a distal end, and the lumen therebetween, and the tool comprises a needle. The method further comprises puncturing a passageway wall at the passageway exit site with the needle. The method further comprises deploying the needle through the passageway wall and through target tissue at a target location beyond the passageway wall. The method further comprises deploying an instrument to perform treatment on the target tissue at the target location. The instrument is deployed within the tool and through a perforation created in the target tissue by the needle.

14 Claims, 10 Drawing Sheets

Related U.S. Application Data

(60) Provisional application No. 62/703,619, filed on Jul. 26, 2018.

(51) Int. Cl.
*A61B 34/35* (2016.01)
*A61B 10/04* (2006.01)
*A61B 18/00* (2006.01)
*A61B 34/20* (2016.01)
*A61B 34/30* (2016.01)
*A61M 25/01* (2006.01)

(52) U.S. Cl.
CPC ............... *A61B 2010/045* (2013.01); *A61B 2017/00115* (2013.01); *A61B 2017/00327* (2013.01); *A61B 2017/3454* (2013.01); *A61B 2018/00285* (2013.01); *A61B 2034/2061* (2016.02); *A61B 2034/301* (2016.02); *A61M 2025/0166* (2013.01)

(58) Field of Classification Search
CPC .. A61B 2018/00285; A61B 2034/2061; A61B 2010/045; A61B 34/35; A61B 2034/301; A61B 18/1492; A61B 34/70; A61B 34/20; A61B 34/30; A61B 18/1477; A61B 10/0233; A61B 2010/0208; A61B 17/34; A61B 10/02; A61B 10/0038; A61B 10/0045; A61B 10/04; A61M 5/32; A61M 25/00; A61M 39/10
See application file for complete search history.

(56) References Cited

U.S. PATENT DOCUMENTS

| | | | |
|---|---|---|---|
| 6,994,094 B2* | 2/2006 | Schwartz | A61B 34/20 600/374 |
| 7,721,742 B2 | 5/2010 | Kalloo et al. | |
| 9,259,317 B2 | 2/2016 | Wilson et al. | |
| 9,993,306 B2 | 6/2018 | Keast et al. | |
| 2004/0215103 A1 | 10/2004 | Mueller, Jr. et al. | |
| 2005/0101837 A1* | 5/2005 | Kalloo | A61B 1/018 600/115 |
| 2009/0287080 A1 | 11/2009 | Nishina et al. | |
| 2010/0249506 A1* | 9/2010 | Prisco | A61B 1/0051 600/117 |
| 2014/0180166 A1* | 6/2014 | Isch | A61M 25/09 600/585 |
| 2015/0223788 A1 | 8/2015 | Walther | |
| 2020/0029948 A1 | 1/2020 | Wong et al. | |

* cited by examiner

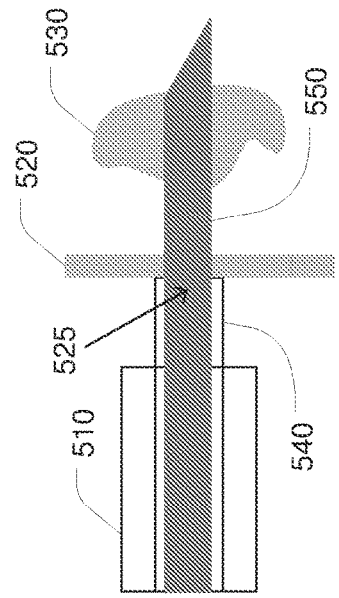
FIG. 5A
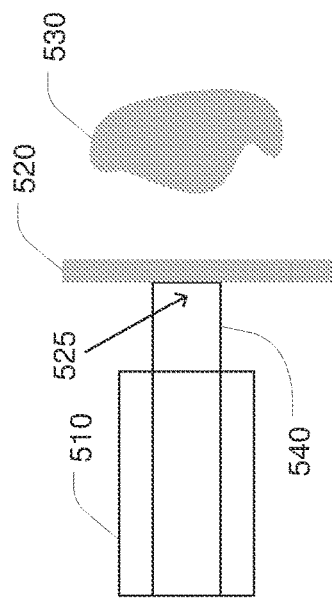
FIG. 5C
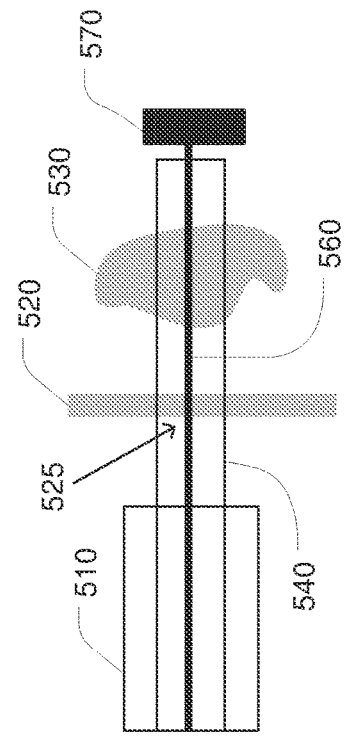
FIG. 5B
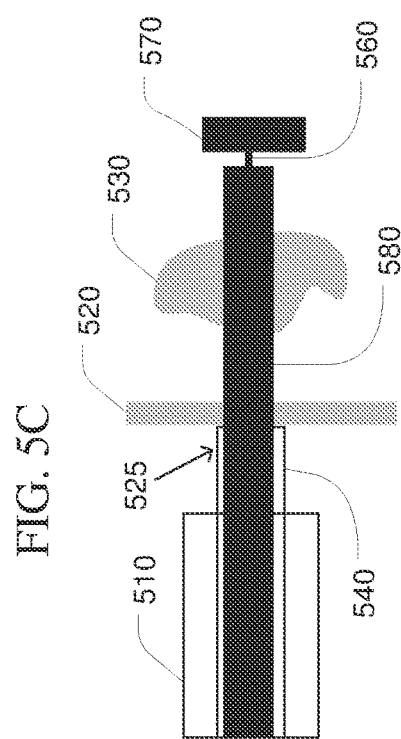
FIG. 5D
FIG. 5E

SYSTEMS AND METHODS OF STEERABLE ELONGATE DEVICE

RELATED APPLICATIONS

This application is the continuation of U.S. patent application Ser. No. 16/523,910, filed Jul. 26, 2019, which claims priority to and the benefit of U.S. Provisional Patent Application No. 62/703,619, filed Jul. 26, 2018 and entitled "Systems and Methods of Steerable Elongate Device," each of which is incorporated by reference herein in its entirety.

FIELD

The present disclosure is directed to systems and methods for controlling a steerable elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach target tissue location. One such minimally invasive technique is to use a flexible and/or steerable elongate device, such as a catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

Accordingly, it would be advantageous to provide input controls that support intuitive control and management of flexible and/or steerable elongate devices, such as steerable catheters, that are suitable for deploying treatment tools to target tissue.

SUMMARY

The embodiments of the invention are best summarized by the claims that follow the description.

Consistent with some embodiments, a method of treating target tissue located among one or more passageways includes deploying a distal end of a flexible elongate device having a lumen along the one or more passageways near a passageway exit site, extending a hollow sheath within the lumen and past the distal end of the flexible elongate device to the passageway exit site, extending a needle within the hollow sheath and to a target location associated with the target tissue, extending the hollow sheath along the needle, retracting the needle from the hollow sheath, deploying a tool to the target location, and performing treatment on the target tissue around the target location using the tool.

Consistent with some embodiments, a method of treating target tissue located among one or more passageways includes deploying a distal end of a flexible elongate device having a lumen along the one or more passageways near a passageway exit site, extending a first hollow sheath within the lumen and past the distal end of the flexible elongate device to the passageway exit site, extending a needle within the first hollow sheath and to a target location associated with the target tissue, retracting the first hollow sheath, extending a second hollow sheath along the needle, retracting the needle from the second hollow sheath, deploying a tool to the target location, and performing treatment on the target tissue around the target location using the tool.

Consistent with some embodiments, a method of treating target tissue located among one or more passageways includes deploying a distal end of a flexible elongate device having a lumen along the one or more passageways near a passageway exit site, extending a tool within the lumen and past the distal end of the flexible elongate device to the passageway exit site and to a target location associated with the target tissue, anchoring the tool, performing treatment on the target tissue around the target location using the tool, removing the anchoring, and retracting the tool.

Consistent with some embodiments, a method of treating target tissue located among one or more passageways includes deploying a distal end of a flexible elongate device having a lumen along the one or more passageways near a passageway exit site, extending a hollow sheath within the lumen and past the distal end of the flexible elongate device to the passageway exit site, extending a needle within the hollow sheath and to a target location associated with the target tissue, extending the hollow sheath along the needle, relaxing at least the distal end of the flexible elongate device, retracting the needle and the sheath, deploying a tool to the target location, and performing treatment on the target tissue around the target location using the tool.

Consistent with some embodiments, a system includes a flexible elongate device and a tool including a first tubular member. The flexible elongate device includes a proximal end, a distal end, and a lumen therebetween. The tool is configured for deployment within the lumen to a passageway exit site, puncturing a passageway wall at the passageway exit site, deployment to a target location, and providing a channel for delivery of an instrument to perform treatment on target tissue around the target location.

BRIEF DESCRIPTIONS OF THE DRAWINGS

FIGS. 5A-5E are simplified diagrams of device configurations during treatment of tissue according to some embodiments.

Figure 1:
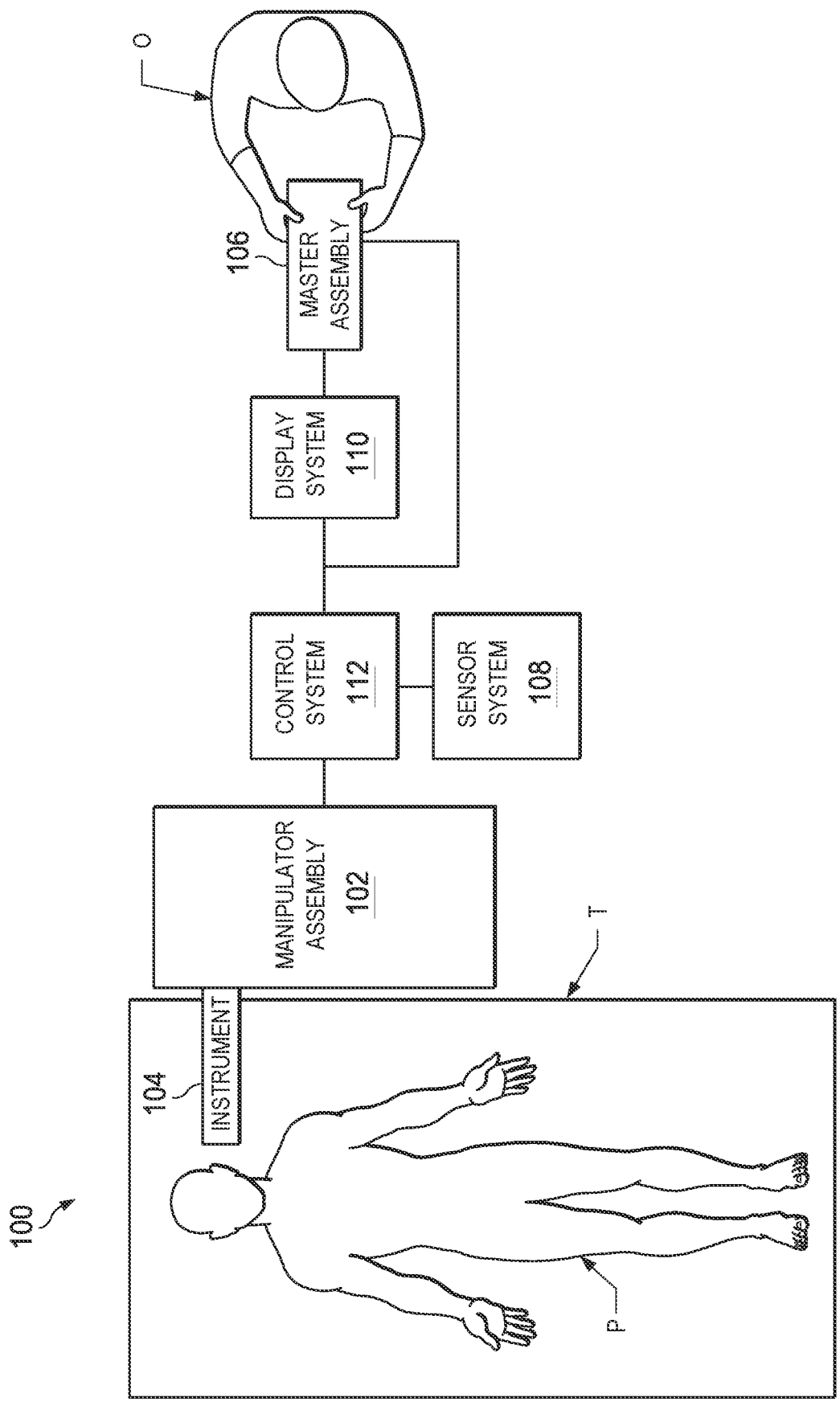
FIG. 1 is a simplified diagram of a teleoperated medical system according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms- such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Various lung bronchoscopic procedures involve navigating an elongate device, such as a flexible catheter, to within proximity of target tissue, such as a lesion or tumor, within the lungs under endoscopic guidance. Once near the target lesion, a procedure can be performed such as a biopsy where a biopsy needle can be delivered within a lumen of the elongate device to obtain a sample of the lesion tissue which is analyzed to, for example, determine whether it is cancerous or non-cancerous. While navigational guidance to the target anatomy is performed with endoscopic visualization and the biopsy is often performed under fluoroscopy, in the case where the lesion is not directly accessible via the bronchial passageways or is otherwise embedded within the parenchymal tissue, it is necessary to penetrate the parenchymal tissue to access the target tissue. This involves navigation of the elongate device to a suitable point of entry where the parenchymal tissue is to be penetrated, penetrating the parenchymal tissue, and then deploying a medical instrument to the target tissue through the parenchymal tissue.

This disclosure focuses primarily on embodiments where the passageways being traversed are airways in lungs. However, one of ordinary skill in the art would understand that these disclosures are equally applicable to other types of passageways that include one or more branch points. For example, other suitable anatomic passageways include vasculature, renal calyces, lymphatic vessels, and/or the like. In other examples, the passageways may correspond to non-anatomic passageways including sewer tunnels, plumbing pipes, conduits, heating ventilation and air conditioning (HVAC) ducts, mines, caves, and/or the like where the penetration of passageway walls and the controlling of leaks is desirable. This disclosure further focuses primarily on embodiments of methods and structures that are directed to the treatment of tissue. However, one of ordinary skill in the art would understand that these disclosures are equally applicable to the treatment of materials other than tissue including materials that may be subject to localized treatment, such as the application of heat and/or other energies.

FIG. 1 is a simplified diagram of a teleoperated medical system 100 according to some embodiments. In some embodiments, teleoperated medical system 100 may be suitable for use in, for example, medical, surgical, diagnostic, therapeutic, or biopsy procedures. In some examples, teleoperated medical system may operate in a non-teleoperational manner under non-teleoperator control. As shown in FIG. 1, medical system 100 generally includes a manipulator assembly 102 for operating a medical instrument 104 in performing various procedures on a patient P. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), a teleoperated kinematic structure, and/or a teleoperational manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. In some embodiments, medical instrument 104 may have a visualization system (discussed in more detail below), which may include a viewing scope assembly that records a concurrent or real-time image of a surgical site and provides the image to the operator O through one or more displays of medical system 100, such as one or more displays of display system 110.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery"); and PCT Patent Application No. PCT/US2016/033596 (filed May 20, 2016) (disclosing "Systems and Methods of Registration for Image Guided Surgery"), each of which is incorporated by reference herein in its entirety, and each disclosing one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly associated with more than one master assembly, and/or more than one non-teleoperational manipulator assembly. The exact number of teleoperational and/or non-teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figures 2A, 2B:
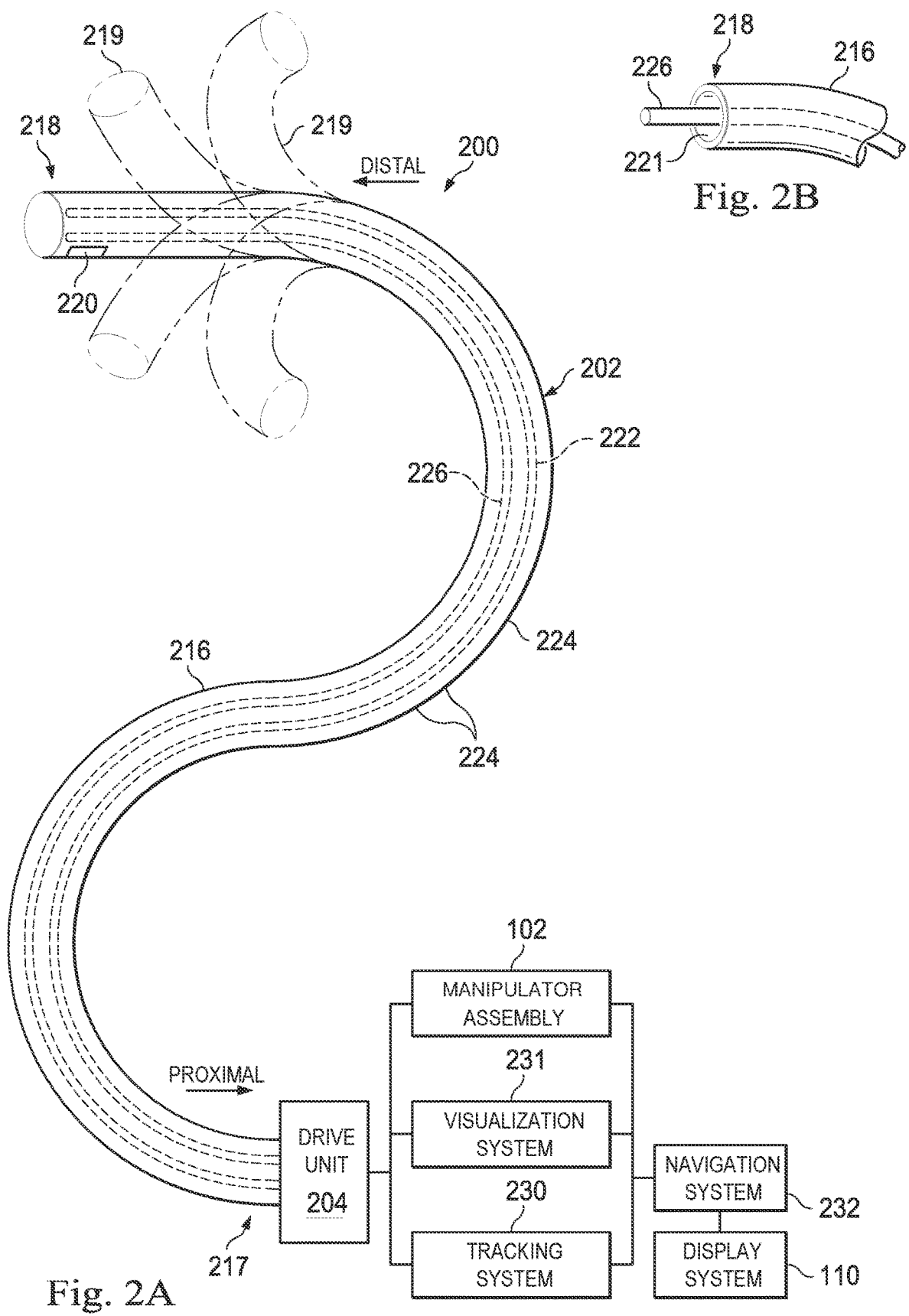
FIG. 2A is a simplified diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. Medical instrument system 200 includes elongate device 202, such as a flexible catheter, coupled to a drive unit 204. Elongate device 202 includes a flexible body 216 having a proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 5,389,187 (filed on Jun. 17, 1998) (disclosing "Optical Fibre Bend Sensor"), which are all incorporated by reference herein in their entireties. Position sensor system 220 may be a component of an EM sensor system with positional sensor system 220 including one or more conductive coils that may be subjected to an externally generated electromagnetic field. Further description of a position sensor system is provided in U.S. Pat. No. 5,380,732 (filed Aug. 11, 1999) (disclosing "Six-Degree of Freedom Tracking System Having a Passive Transponder on the Object Being Tracked"), which is incorporated by reference herein in its entirety. Alternatively, position sensor system 220 may include other types of localization sensors including impedance based sensors, ultrasound sensors, time of flight based sensors, and/or the like.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may further be used in conjunction with one or more sensors to support a desired procedure. The one or more sensors may include sensors to aid in the location of target tissue, avoid contact with or damage to tissue to be avoided, detect undesirable bleeding, and/or the like. The one or more sensors may include one or more Doppler devices, such as Doppler OCT or Doppler ultrasound, monoscopic or stereoscopic imaging sensors, such as a fiber optic bundle, a fiberscope, an endoscope, an optical coherence tomography (OCT) device, ultrasound transducers, and/or the like. The one or more imaging sensors may include one or more cables or optical fibers coupling the one or more imaging sensors to visualization system 231. The one or more imaging sensors may be single or multi-spectral, for example capturing image data in one or more of the visible, infrared, and/or ultraviolet spectrums using techniques such as Fourier transform spectroscopy, Raman Spectroscopy, and/or the like. Alternatively, medical instrument 226 may itself be an image capture probe to which the one or more imaging sensors are mounted. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

In some embodiments, teleoperated medical instrument system 200 can be used to access and treat target tissue such as tumors providing an alternative to currently available manual procedures for treatment of malignant nodules. One currently available manual procedure includes surgery which is highly invasive so can result in high morbidity, mortality, and long-term impacts on patient quality of life. And not all patients are good candidates for surgery due specific physiology contributing to health issues. Stereotactic Body Radiation Therapy (SBRT) is a non-invasive treatment modality but can result in radiation side effects and limited ability to retreat during recurrence due to a lifetime toxicity limit. Ablation modalities, such as RF is largely delivered percutaneously so includes a risk of pneumothorax. Additionally, these ablation modalities have seen limited effectiveness due to incomplete ablation. Thus there is a need for a minimally invasive treatment which can be provided using a robotic medical system.

Figure 3:
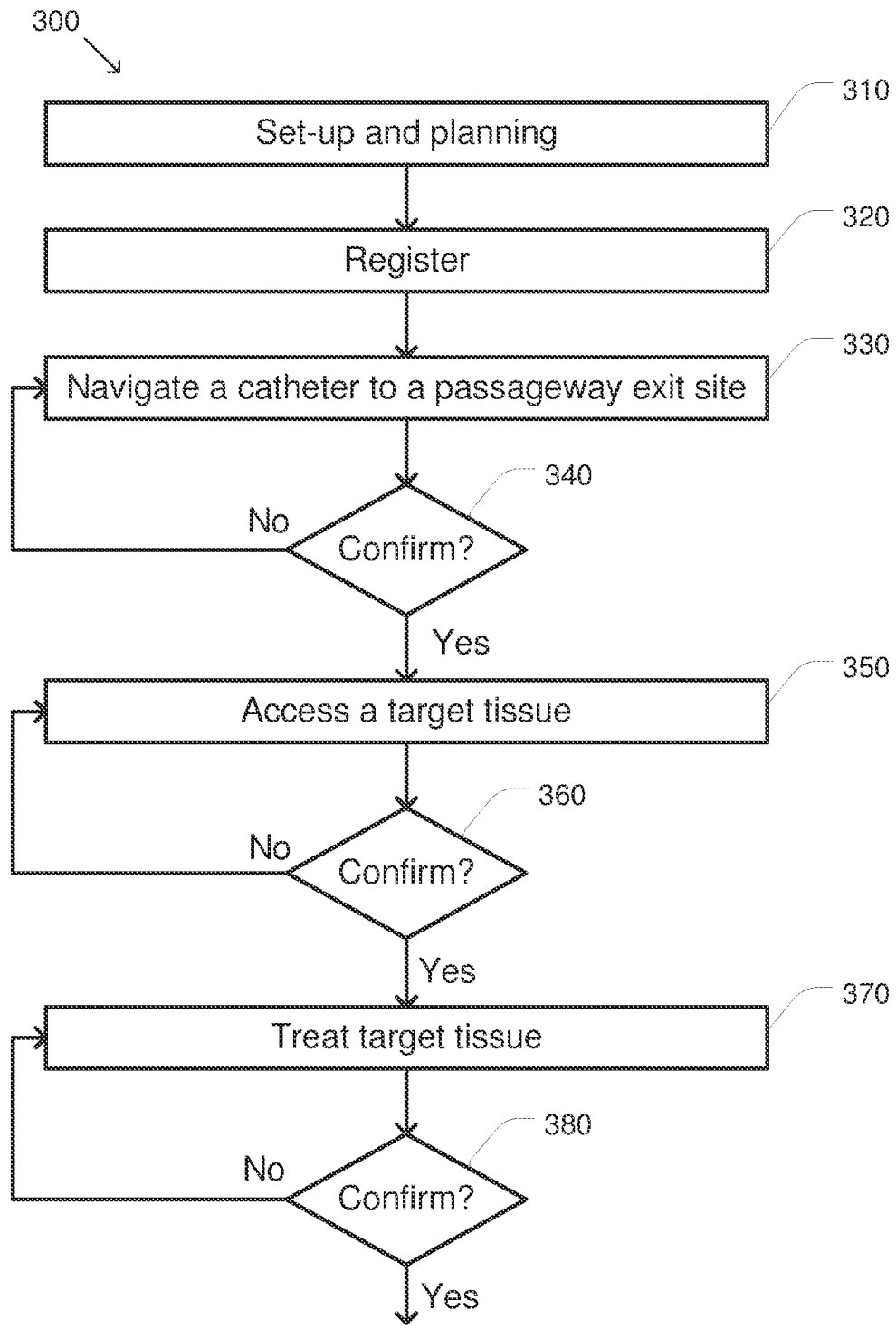
FIG. 3 is a simplified diagram of a method of treating tissue according to some embodiments.

FIG. 3 is a simplified diagram of a method 300 of treating tissue according to some embodiments. One or more of the processes 310-380 of method 300 may be implemented, at least in part, in the form of executable code stored on non-transitory, tangible, machine-readable media that when run by one or more processors (e.g., a processor in control system 112) may cause the one or more processors to perform one or more of the processes 310-380. In some embodiments, one of process 340 or process 360 may be omitted. In some embodiments, processes 370 and 380 may be performed concurrently and/or process 380 may be omitted. In some embodiments, method 300 may be used to deploy various tools, instruments, devices, and/or the like through one or more passageways in order to perform a treatment on target tissue, such as a tumor or lesion in anatomical tissue and/or the like.

At a process 310, set-up and planning occur. In some examples, the set-up and planning may include obtaining one or more pre-procedure images of the one or more passageways and/or the target tissue. In some examples, the one or more pre-procedure images may include one or more x-rays, one or more fluoroscopic images, one or more ultrasound images, one or more computer-aided tomographic (CT) images, one or more magnetic resonance imaging (MRI) images, and/or the like. In some examples, the set-up and planning may include planning a route through the one or more passageways to a location near the target tissue and/or, in cases where the target is located within the passageway wall and/or within tissue distal to the passageway wall, determining one or more exit sites from the one or more passageways to obtain access to the target tissue. In some examples, the set-up and planning may include determining one or more tools, instruments, devices, and/or the like that are suitable for performing the treatment procedure.

At a process 320, the catheter is registered to the one or more pre-procedure images. In some examples, registration can be performed by steering or articulating the catheter through portions of anatomy while tracking the position of a distal end, or portion of the catheter. In some examples, the catheter may be tracked using tracking system 230 and one or more of the techniques described with respect to FIG. 2. In some examples, the catheter may be steered with the aid of visualization system 231. Registration is described in more detail in commonly owned PCT Patent Application No. PCT/US18/12969 (filed Jan. 9, 2018) (disclosing "Systems And Methods For Registering Elongate Devices To Three-Dimensional Images In Image-Guided Procedures"), which is incorporated by reference herein in its entirety.

At a process 330, a catheter is navigated to a passageway exit site. In some examples, the catheter may be a flexible elongate device consistent with elongate device 202 and may include one or more lumens for deploying one or more tools, instruments, devices, and/or the like to a distal end of the catheter. In some examples, the catheter may be navigated through the one or more passageways, such that a distal end of the catheter is positioned at a location near the passageway exit site in an orientation aligning the distal end towards the target tissue. In some examples, the planning of process 310 may be used during the navigation. In some examples, the catheter may be tracked during the navigation using tracking system 230 and/or under direct visualization using one or more of the techniques previously described. In some examples, the catheter may further be parked at the location near the passageway exit with the aligning orientation by locking and/or braking the actuating mechanisms at the proximal end of the catheter used to navigate and/or steer the catheter. In some examples, the actuating mechanisms may be consistent with the mechanisms of drive unit 204.

At a process 340, it is confirmed whether the distal end of the catheter is located near the passageway exit site and suitably aligned toward the target tissue. In some examples, tracking system 230 and/or visualization system 231 may be used to confirm whether the distal end of the catheter is suitably positioned and/or aligned. In some examples, the confirming may be performed by obtaining one more intra-procedure images, such as by obtaining one or more CT images (e.g., using a cone-beam CT system and/or the like), one or more ultrasound images (e.g., using one or more EBUS transducers), and/or the like. In some examples, the confirming may be used to make any corrections to the location and/or orientation of the distal end of the catheter due to movement of the one or more passageways and/or movement of the target tissue since the pre-procedure images were obtained (e.g., due to anatomical movement), errors in the registration of process 340, and/or the like. When the distal end of the catheter is not suitably positioned or suitably aligned, processes 330 and 320 are repeated by returning to process 330. When the distal end of the catheter is suitably positioned and suitably aligned, method 300 continues beginning with a process 350. In some embodiments, the confirming may include segmentation and processing similar to the segmentation and processing completed during a pre-operative planning step such as process 310.

At the process 350, access to the target tissue is obtained. One or more tools, instruments, devices, and/or the like are deployed through the one or more lumens of the catheter to gain access to the target tissue through a wall of the one or more passageways at the passageway exit site so that a tool may be deployed to the target tissue and a treatment of the tissue may be performed as described further with respect to process 370. Process 350 is described in more detail with respect to FIGS. 4-12. Examples of accessing target tissue from one or more passageways are described in more detail in commonly owned PCT Patent Application No. PCT/US18/017621 (filed Feb. 9, 2018) (disclosing "Systems and Methods of Accessing Encapsulated Targets"), which is incorporated by reference herein in its entirety. Process 350 is described in more detail with respect to FIGS. 4-12.

At a process 360, it is confirmed whether the one or more tools, instruments, and/or devices are positioned within or near the target tissue. In some examples intra-operative imaging may be used to confirm whether one or more tools, instruments, and/or devices are appropriately positioned and/or oriented relative to the target tissue. In some examples, the confirming may be performed by obtaining one more intra-procedure images, such as by obtaining one or more CT images (e.g., using a cone-beam CT system and/or the like), one or more ultrasound images (e.g., using one or more EBUS transducers), and/or the like. In some examples, the images may be obtained while the one or more tools, instruments, and/or devices are positioned in the target tissue and/or in succession as the one or more tools, instruments, and/or devices are being positioned to access the target tissue (e.g., when the image are obtained using one or more EBUS transducers). In some embodiments, the one or more tools, instruments, and/or devices may be used to confirm whether the one or more tools, instruments, and/or devices are within and/or near the target tissue (e.g., by measuring the resonant frequency, impedance, and/or the like of a microwave antenna). In some embodiments, the modality used for the confirming may depend on a level of certainty desired for confirming whether the one or more tools, instruments, and/or devices are positioned within or near the target tissue. In some examples, using the one or more tools, instruments, and/or devices provide a lower level of certainty than the use of an imaging modality based on ultrasound, OCT, and/or microscopy. In some examples, an imaging modality based on CT, cone-beam CT, and/or the like provides the greatest certainty. In some examples, the choice of modality may be made based on the costs of performing the confirming with use of the one or more tools, instruments, and/or devices having the lowest relative cost, use a secondary sensor (e.g., for ultrasound, OCT, microscopy, and/or the like) having a higher cost, and use of a full visualization system (e.g., CT, cone-beam CT, and/or the like) having a highest cost. In some examples, the confirming may be used to make any corrections to the position and/or orientation of the one or more tools/instruments/devices due to movement of the target tissue (e.g., due to anatomical movement, shift in target, etc.), errors in the registration of process 310, process 340, and/or the like. If the position and/or orientation of the one or more tools, instruments, and/or devices are not confirmed, the one or more tools/instruments/devices are retracted, the catheter is re-positioned and process 340, 350, and 360 are repeated. When position of the one or more tools/instruments/devices are confirmed, method 300 continues beginning with a process 370.

At a process 370, the tool is used to treat the target tissue. In some examples, the treatment may include taking a sample (or biopsy) of the target tissue. In some examples, the treatment may include introducing one or more chemicals to the target tissue. In some examples, the one or more chemicals may include an ablation accelerant, a therapeutic drug (e.g., a chemotherapy agent), a radioactive tissue treatment (e.g., a radiation treatment and/or marking agent), and/or the like. In some examples, the one or more chemicals may be injected. In some examples, the treatment may include ablation, including one or more of RF, microwave, ultrasound, HIFU, direct heat, cryo, chemical ablation and/or the like. In some examples, the treatment may include obtaining images and/or other sensor readings (e.g. temperature measurements, inductance measurements, etc.) from the target tissue. In some examples, the imaging may be performed using one or more ultrasound transducers, such as EBUS transducers, Doppler transducers, and/or the like.

At a process 380, it is confirmed whether the treatment of the target tissue is complete. In some examples, visualization system 231, one or more intra-procedural images, and/or the like may be used to determine whether treatment of the target tissue is complete. In some examples, the one or more images may include one or more x-rays, one or more fluoroscopic images, one or more ultrasound images, one or more CT/CAT images, one or more MRI images, and/or the like. In some examples, when the treatment of process 370 includes the introduction of energy (e.g., during an ablative procedure), one or more of impedance profiles, temperature profiles, frequency responses, and/or the like may be monitored to confirm whether the treatment of the target tissue is confirmed. When the treatment of the target tissue is not complete, treatment continues by returning to process 370. When the treatment of the tissue is complete, method 300 ends.

Figure 4:
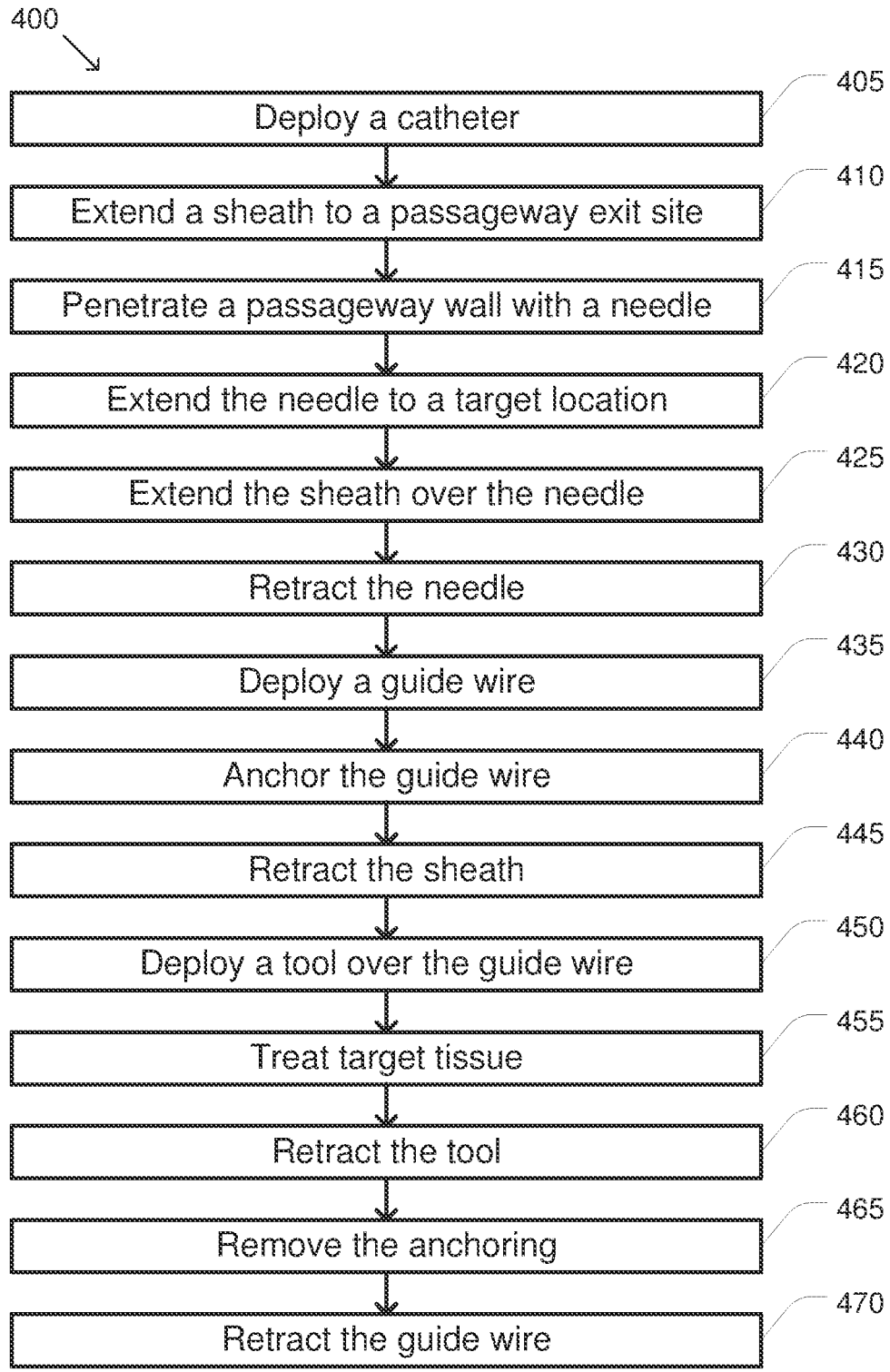
FIG. 4 is a simplified diagram of a method of treating tissue according to some embodiments.

FIG. 4 is a simplified diagram of a method 400 of treating tissue according to some embodiments. One or more of the processes 405-470 of method 400 may be implemented, at least in part, in the form of executable code stored on non-transitory, tangible, machine-readable media that when run by one or more processors (e.g., a processor in control system 112) may cause the one or more processors to perform one or more of the processes 405-470. In some embodiments, processes 440 and 465 are optional and may be omitted. In some embodiments, method 400 may include other processes (not shown), such as processes corresponding to one or more of processes 310, 320, 340, 360, and/or 380 of method 300. In some embodiments, method 400 may be used to deploy various tools, instruments, devices, and/or the like through one or more passageways in order to perform a treatment on target tissue, such as a tumor or lesion in anatomical tissue and/or the like.

At a process 405, a catheter is deployed and positioned at a location proximate target tissue. In some examples, the catheter may be consistent with elongate device 202 and may include one or more lumens for deploying one or more tools, instruments, devices, and/or the like to a distal end of the catheter. In some examples, the catheter may be navigated through the one or more passageways to a location near the passageway exit site with an orientation of the distal end of the catheter aligned toward the target tissue. In some examples, process 405 may be substantially the same as process 330 and may include processes 310 and/or 320.

At a process 410, a sheath (e.g., a tubular member) is extended to the passageway exit site. The sheath may be an elongate, flexible device including a lumen or channel. In some examples, the sheath may be extended though one of the one or more lumens of the catheter until a distal end of the sheath reaches the passageway exit site, positioning the distal end of the sheath into contact with the passageway wall at the passageway exit site. In some examples, the sheath may be extended toward the passageway exit site along an orientation axis consistent with the orientation of the distal end of the catheter. In some examples, the distal end of the sheath may be angled relative to the orientation of the distal end of the catheter (e.g., by steering using cables, linkages, or other steering controls similar to those used to steer elongate device 202 and/or the catheter during process 405, using a memory alloy, and/or the like) so as to align the distal end of the sheath perpendicular to the passageway wall at the passageway exit site. In some examples, the distal end of the sheath includes one or more barbs, teeth, tines, cleats, and/or the like to prevent the distal end of the sheath from slipping, skiving, and/or the like away from the passageway exit site. In some examples the sheath may be pre-shaped to help situate the sheath against the passageway wall at the passageway exit site.

FIG. 5A is a simplified diagram of device configuration after the completion of process 410 according to some embodiments. FIG. 5A shows a catheter 510 deployed within a passageway so that it is in proximity to a passageway wall 520 at a passageway exit site 525 and is further oriented toward target tissue 530 located within the tissue distal to passageway exit site 525. Also shown is a sheath 540 (e.g., a tubular member) extended beyond a distal end of catheter 510 so that a distal end of sheath 540 is in contact with passageway wall 520 at passageway exit site 525.

Referring back to FIG. 4, at a process 415 the passageway wall at the passageway exit site is penetrated using a needle. The needle is extended through the lumen of the sheath and is used to penetrate through the passageway wall at the passageway exit site.

At a process 420, the needle is extended to a target location. In some examples, the needle may be extended beyond the passageway wall until it reaches the target tissue and/or extends beyond the target tissue.

FIG. 5B is a simplified diagram of device configuration after the completion of process 420 according to some embodiments. FIG. 5B shows a needle 550 extended through passageway wall 520 at passageway exit site 525 and through intervening tissue until needle 550 is extended through target tissue 530. And although FIG. 5B shows that needle 550 is extended completely through target tissue 530, in other embodiments, needle 550 may alternatively be extended to just before target tissue 530 and/or partially through target tissue 530 instead of completely through target tissue 530. And although needle 540 is shown with a beveled distal end, other shapes for the distal end of needle 540 are possible, including one or more of a conical distal end, a cross cut distal end, a distal end with one or more crown points, a distal end with one or more bent crown points, and/or the like.

Referring back to FIG. 4, at a process 425 the sheath is extended over the needle. In some examples, the sheath is extended over the needle until the distal end of the sheath is located approximately at the distal end of the needle. In some examples, the sheath is extended over the needle to prevent the tissue between the passageway exit site and the distal end of the needle from collapsing when the needle is retracted.

FIG. 5C is a simplified diagram of device configuration after the completion of process 425 according to some embodiments. FIG. 5C shows sheath 540 extended so that the distal end of sheath 540 is approximately at the distal end of needle 550.

Referring back to FIG. 4, at a process 430, the needle is retracted. In some examples, the needle is retracted completely from the sheath and the catheter so that the lumen of the sheath may be used to deploy one or more other tools, instruments, devices, and/or the like. The sheath continues to serve as a conduit through from the passageway exit site to or through the target tissue At a process 435, a guide wire is deployed through the lumen of the sheath to the distal end of the sheath and/or just beyond the distal end of the sheath.

At an optional process 440, the guide wire is anchored. In some examples, the guide wire is anchored by inflating one or more balloons located at a distal end of the guide wire. In some examples, the one or more balloons are inflated by injecting a gas, a fluid, and/or the like through a lumen of the guide wire. In some examples, the one or more balloons are inflated to a size that provides sufficient stability for the guide wire. In some examples, the one or more balloons are inflated to a size that is at least as large as the distal opening of the sheath. In some examples, the one or more balloons anchor the distal end of the guide wire so that the distal end of the guide wire remains effectively stationary after the sheath is retracted.

FIG. 5D is a simplified diagram of device configuration after the completion of processes 435 and 440 according to some embodiments. FIG. 5D shows a guide wire 560 extended beyond the distal end of sheath 540. FIG. 5D further shows one or more balloons 570 inflated so as to anchor a distal end of guide wire 560.

Referring back to FIG. 4, at a process 445, the sheath is retracted. In some examples, the sheath is retracted at least to the passageway exit site so that the lumen of the sheath may continue to be used to deploy one or more other tools, instruments, devices, and/or the like. In some examples, the sheath is retracted to a proximal end of the catheter and removed completely from the catheter.

At a process 450, a tool is deployed over the guide wire to the target tissue. In some examples, the tool is extended until a distal end of the tool is near the distal end of the guide wire. In other examples, the tool is extended along the guide wire so the distal end of the tool is positioned partially within the target tissue. In some examples, the tool may be an ablation tool, an imaging device, a sensor, and/or the like.

FIG. 5E is a simplified diagram of device configuration after the completion of process 450 according to some embodiments. FIG. 5E shows a tool 580 deployed along guide wire 560 so that tool 580 has fully penetrated and is in contact with target tissue 530 and the distal end of the tool is positioned within non-target tissue.

Referring back to FIG. 4, at a process 455, the target tissue is treated. In some examples, the treatment of the target tissue may include using the tool 580 to deliver ablative energy including one or more of RF ablation, microwave ablation, and/or the like. In some examples, the treatment of the target tissue may be confirmed by obtaining images and/or other sensor readings from the target tissue. In some examples, the imaging may be performed using one or more ultrasound transducers, such as EBUS transducers, Doppler transducers, and/or the like. In some examples, process 455 may be substantially the same as process 370.

At a process 460, the tool is retracted. In some examples, the tool is retracted to a point proximal to the passageway wall at the passageway exit site. In some examples, the tool is retracted so that it is completely within the sheath and/or the catheter. In some examples, the tool is retracted to the proximal end of the sheath and the catheter and removed from the sheath and the catheter.

At an optional process 465, when the anchoring of the guide wire occurred during process 440, the anchoring is removed. In some examples, the anchoring may be removed by evacuating the gas, fluid, and/or the like from the one or more balloons using vacuum and/or suction through the lumen within the guide wire.

At a process 470, the guide wire is retracted. In some examples, the guide wire is retracted to a point proximal to the passageway wall at the passageway exit site. In some examples, the guide wire is retracted so that it is completely within the sheath and/or the catheter. In some examples, the guide wire is retracted to the proximal end of the sheath and/or the catheter and completely removed from the sheath and/or the catheter.

As discussed above and further emphasized here, FIG. 4 is merely an example which should not unduly limit the scope of the claims. One of ordinary skill in the art would recognize many variations, alternatives, and modifications. According to some embodiments, one or more of processes 405-470 may be performed in orders other than those implied by FIG. 4. In some examples, process 445 may be performed after process 440 so that the sheath may be used to help deploy the tool. In some examples, process 460 may be performed after process 465 and/or processes 460 and 470 may be performed substantially concurrently after process 465 so that the tool and the guide wire may be retracted concurrently after the optional anchoring is removed.

Figure 6:
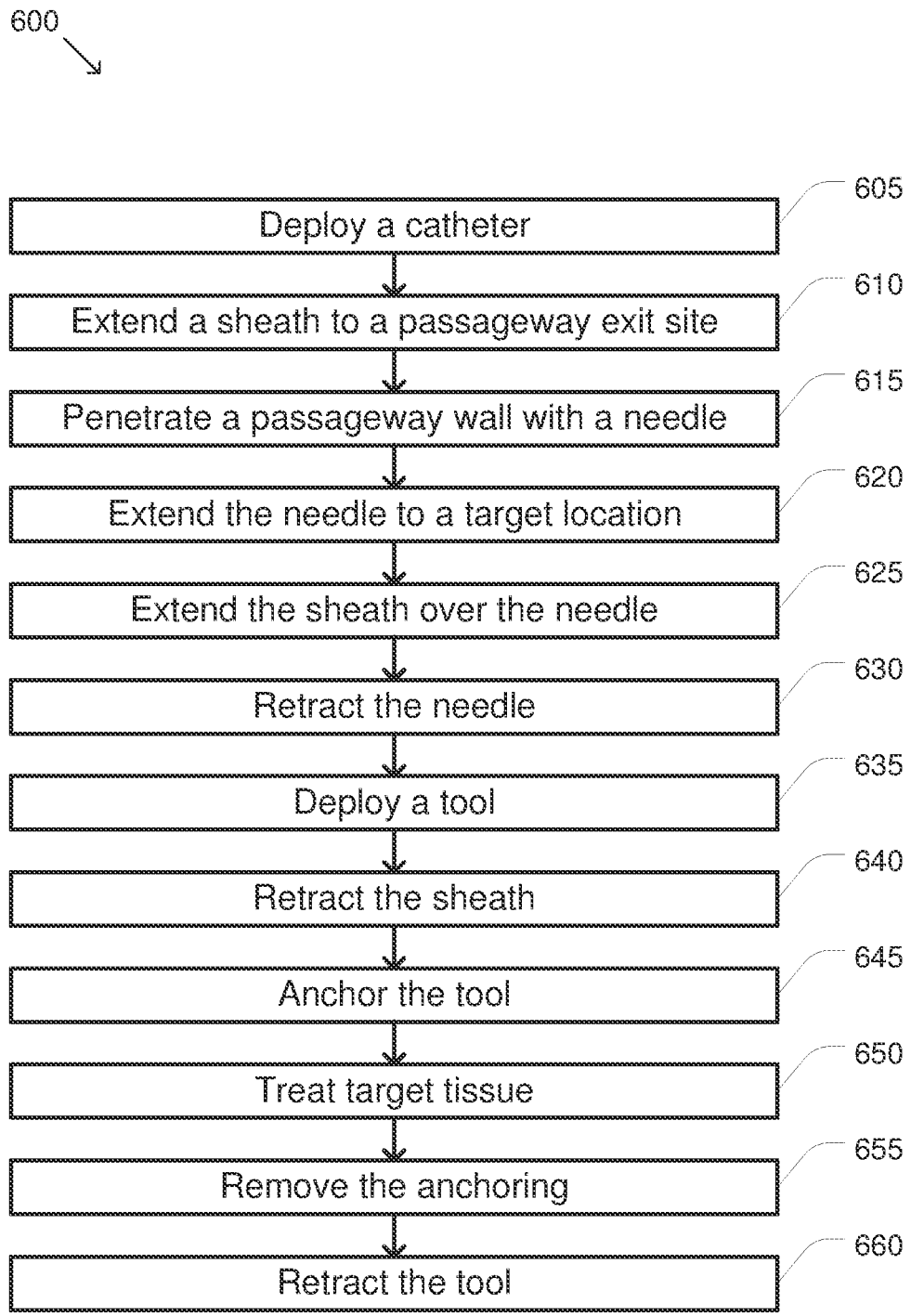
FIG. 6 is a simplified diagram of a method of treating tissue according to some embodiments.

FIG. 6 is a simplified diagram of a method 600 of treating tissue according to some embodiments. One or more of the processes 605-660 of method 600 may be implemented, at least in part, in the form of executable code stored on non-transitory, tangible, machine-readable media that when run by one or more processors (e.g., a processor in control system 112) may cause the one or more processors to perform one or more of the processes 605-660. In some embodiments, processes 645 and 655 are optional and may be omitted. In some embodiments, method 600 may include other processes (not shown), such as processes corresponding to one or more of processes 310, 320, 340, 360, and/or 380 of method 300. In some embodiments, method 600 may be used to deploy various tools, instruments, devices, and/or the like through one or more passageways in order to perform a treatment on target tissue, such as a tumor or lesion in anatomical tissue and/or the like.

According to some embodiments, processes 605-630 may be substantially the same as corresponding processes 405-430 of method 400.

At a process 635, a tool is deployed. In some examples, the tool may be deployed by inserting the tool through the lumen of the sheath so that a distal end of the tool reaches the target tissue and/or extends beyond the target tissue. In some examples, the distal end of the tool may be extended to a point proximal to the distal end of the sheath, to the distal end of the sheath, and/or beyond the distal end of the sheath.

At a process 640, the sheath is retracted. In some examples, the sheath is retracted at least to the passageway exit site so that the lumen of the sheath may continue to be used to deploy one or more other tools, instruments, devices, and/or the like. In some examples, the sheath is retracted to a proximal end of the catheter and removed from the catheter. In some examples, process 640 may be substantially the same as process 445.

At a process 645, the tool is anchored. In some examples, the tool may be anchored to prevent undesirable movement of the tool during treatment of the tissue. In some examples, the anchoring may include deploying an anchoring device near the distal end of the tool, along a length of the tool, and/or the like. In some examples, the anchoring device may include one or more balloons located at the distal end of the tool and/or along the length of the tool. In some examples, the one or more balloons are inflated by injecting a gas, a fluid, and/or the like through a lumen of the tool. In some examples, the one or more balloons are inflated to anchor corresponding portions of the tool (e.g., the distal end and/or one more locations along the length of the tool and proximal to the distal end) so that the corresponding portions remains effectively stationary during treatment of the target tissue. In some examples, the anchoring device may include one or more memory alloy barbs and/or the like located at the distal end of the tool and/or along the length of the tool. In some examples, the one or more barbs are deployed to anchor the tool within the target tissue. In some examples, process 645 is substantially the same as process 360.

Figure 7:
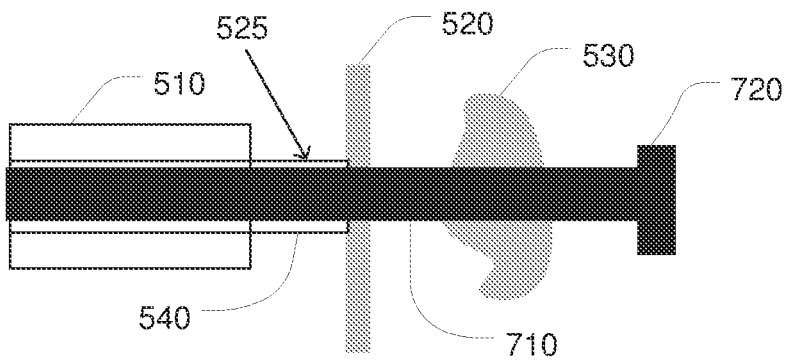
FIG. 7 is a simplified diagram of device configurations during treatment of tissue according to some embodiments.

FIG. 7 is a simplified diagram of device configuration after the completion of the optional process 645 according to some embodiments. FIG. 7 shows a tool 710 deployed through catheter 510 and sheath 540 through passageway wall 520 and through target tissue 530 so that tool 710 is in contact with target tissue 530. FIG. 7 further shows that sheath 540 is retracted to a point proximal to passageway exit site 525 of passageway wall 520. And although FIG. 7 shows that tool 710 is extended completely through target tissue 530, in other embodiments, tool 710 may alternatively be extended to just before target tissue 530 and/or partially through target tissue 530 instead of completely through target tissue 530. FIG. 7 further shows embodiments where the anchoring device is one or more balloons 720 located at a distal end of tool 710. However, other embodiments are possible where the anchoring device is one or more balloons located along a length of tool 710, one or more barbs located at the distal end of tool 710, one or more barbs located along the length of tool 710, and/or the like.

Referring back to FIG. 6, at a process 650, the target tissue is treated. In some examples, process 650 may be substantially the same as process 370 and/or process 455.

At an optional process 655, when the anchoring of the tool occurred during process 645, the anchoring is removed. In some examples, when the anchoring device included one or more balloons, the anchoring may be removed by evacuating the gas, fluid, and/or the like from the one or more balloons using the lumen within the tool. In some examples, when the anchoring device included one or more barbs, the one or more barbs may be retracted by, in part, extending the sheath back over the tool until the distal end of the sheath is extended beyond the most distal of the barbs.

At a process 660, the tool is retracted. In some examples, process 660 may be substantially the same as process 460.

As discussed above and further emphasized here, FIG. 6 is merely an example which should not unduly limit the scope of the claims. One of ordinary skill in the art would recognize many variations, alternatives, and modifications. According to some embodiments, one or more of processes 605-660 may be performed in orders other than those implied by FIG. 6. In some examples, the tool may be deployed without using the sheath by performing process 640 before process 635.

Figure 8:
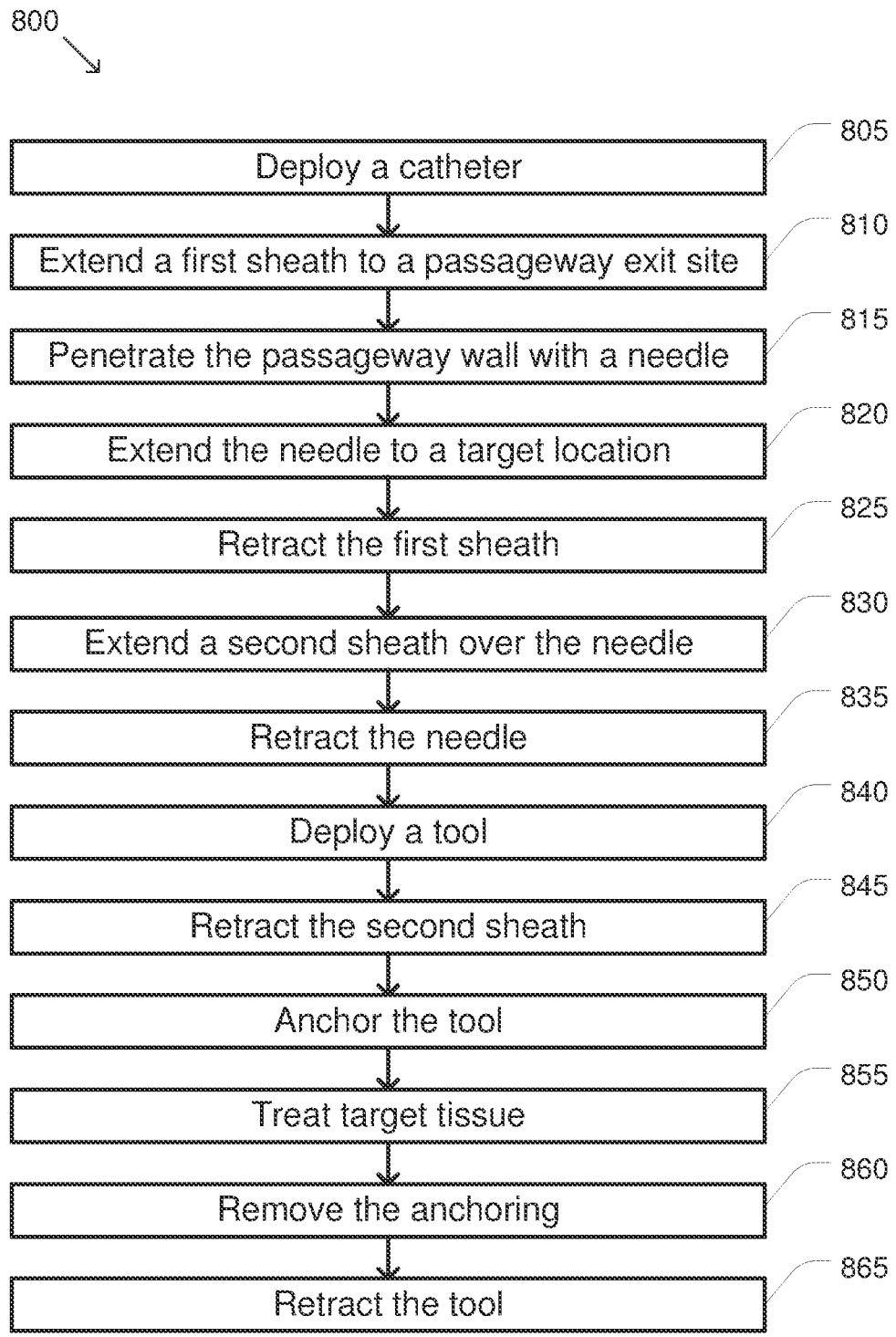
FIG. 8 is a simplified diagram of a method of treating tissue according to some embodiments.

FIG. 8 is a simplified diagram of a method 800 of treating tissue according to some embodiments. One or more of the processes 805-865 of method 800 may be implemented, at least in part, in the form of executable code stored on non-transitory, tangible, machine-readable media that when run by one or more processors (e.g., a processor in control system 112) may cause the one or more processors to perform one or more of the processes 805-865. In some embodiments, process 850 may be performed before process 845. In some embodiments, processes 850 and 860 are optional and may be omitted. In some embodiments, method 800 may include other processes (not shown), such as processes corresponding to one or more of processes 310, 320, 340, 360, and/or 380 of method 300. In some embodiments, method 800 may be used to deploy various tools, instruments, devices, and/or the like through one or more passageways in order to perform a treatment on target tissue, such as a tumor or lesion in anatomical tissue and/or the like.

At a process 805, a catheter is deployed. In some examples, process 805 may be substantially the same as process 330, process 405, and/or process 605.

At a process 810, a first sheath is extended to a passageway exit site. In some examples, process 810 may be substantially the same as process 410 and/or process 610, but with respect to the first sheath.

At a process 815, the passageway wall at the passageway exit site is penetrated using a needle. In some examples, process 815 may be substantially the same as process 415 and/or process 615.

At a process 820, the needle is extended to a target location. In some examples, process 820 may be substantially the same as process 420 and/or process 620.

At a process 825, the first sheath is retracted. In some examples, the first sheath is retracted to a proximal end of the catheter and removed from the catheter so as to make room in the lumen of the catheter for a second sheath.

At a process 830, the second sheath is extended over the needle. In some examples, an inner diameter of a lumen of the second sheath is larger than an inner diameter of a lumen of the first sheath so as to be able to support a tool with a cross section larger than a cross section that is supported by the first sheath. Using a process similar to process 425 and/or process 625, the second sheath is extended over the needle. In some examples, the second sheath is extended over the needle until a distal end of the second sheath is located approximately at the distal end of the needle. In some examples, the second sheath is extended over the needle to prevent the tissue between the passageway exit site and the distal end of the needle from collapsing when the needle is retracted.

Figure 9A:
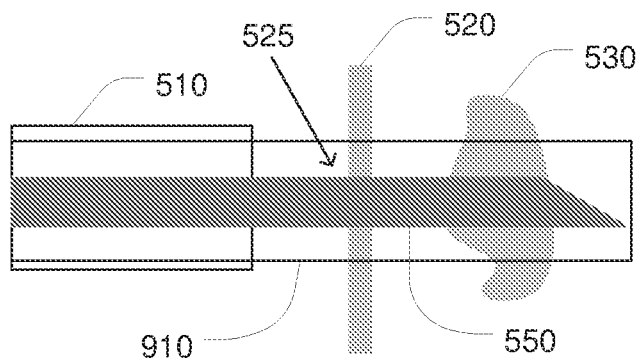
FIGS. 9A and 9B are simplified diagrams of device configurations during treatment of tissue according to some embodiments.

FIG. 9A is a simplified diagram of device configuration after the completion of process 830 according to some embodiments. FIG. 9A shows a second sheath 910 extended so that the distal end of second sheath 910 is approximately at the distal end of needle 550.

Referring back to FIG. 8, at a process 835, the needle is retracted. In some examples, process 835 may be substantially the same as process 430 and/or process 630.

At a process 840, a tool is deployed. In some examples, the tool may be deployed by inserting the tool through the lumen of the second sheath so that a distal end of the tool reaches the target tissue and/or extends beyond the target tissue. In some examples, the distal end of the tool may be extended to a point proximal to the distal end of the second sheath, to the distal end of the second sheath, and/or beyond the distal end of the second sheath.

At a process 845, the second sheath is retracted. In some examples, the second sheath is retracted at least to the passageway exit site so that the lumen of the second sheath may continue to be used to deploy one or more other tools, instruments, devices, and/or the like. In some examples, the second sheath is retracted to a proximal end of the catheter and completely removed from the catheter. In some examples, process 845 may be substantially the same as process 445 and/or process 640.

At an optional process 850, the tool is anchored. In some examples, process 850 is substantially the same as process 360 and/or process 645.

Figure 9B:
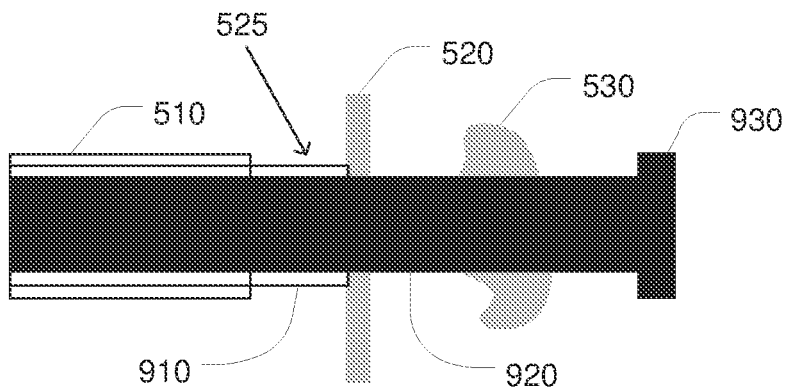

FIG. 9B is a simplified diagram of device configuration after the completion of the optional process 850 according to some embodiments. FIG. 9B shows a tool 920 deployed through catheter 510 and second sheath 910 through passageway wall 520 and through target tissue 530 so that tool 920 is in contact with target tissue 530. FIG. 9B further shows that second sheath 910 is retracted to a point proximal to passageway exit site 525 of passageway wall 520. And although FIG. 9B shows that tool 920 is extended completely through target tissue 530, in other embodiments, tool 920 may alternatively be extended to just before target tissue 530 and/or partially through target tissue 530 instead of completely through target tissue 530. FIG. 9B further shows embodiments where the anchoring device is one or more balloons 930 located at a distal end of tool 920. However, other embodiments are possible where the anchoring device is one or more balloons located along a length of tool 920, one or more barbs located at the distal end of tool 920, one or more barbs located along the length of tool 920, and/or the like.

Referring back to FIG. 8, at a process 855, the target tissue is treated. In some examples, process 855 may be substantially the same as process 370, process 455, and/or process 650.

At an optional process 860, when the anchoring of the tool occurred during process 850, the anchoring is removed. In some examples, when the anchoring device included one or more balloons, the anchoring may be removed by evacuating the gas, fluid, and/or the like from the one or more balloons using the lumen within the tool. In some examples, when the anchoring device included one or more barbs, the one or more barbs may be retracted by, in part, extending the second sheath back over the tool until the distal end of the second sheath is extended beyond the most distal of the barbs.

At a process 865, the tool is retracted. In some examples, process 865 may be substantially the same as process 460 and/or process 660.

As discussed above and further emphasized here, FIG. 8 is merely an example which should not unduly limit the scope of the claims. One of ordinary skill in the art would recognize many variations, alternatives, and modifications. According to some embodiments, one or more of processes 805-865 may be performed in orders other than those implied by FIG. 8. In some examples, the tool may be deployed without using the second sheath by performing process 845 before process 840.

Figure 10:
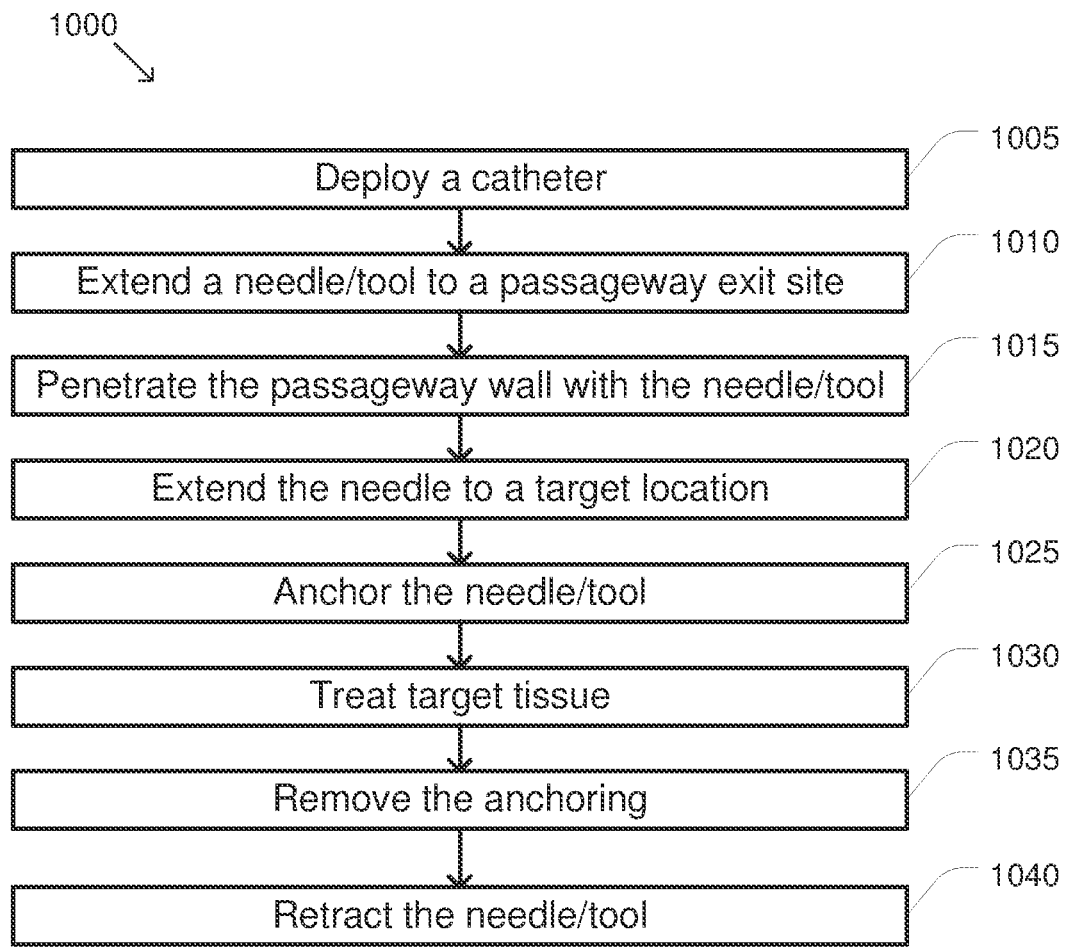
FIG. 10 is a simplified diagram of a method of treating tissue according to some embodiments.

FIG. 10 is a simplified diagram of a method 1000 of treating tissue according to some embodiments. One or more of the processes 1005-1040 of method 1000 may be implemented, at least in part, in the form of executable code stored on non-transitory, tangible, machine-readable media that when run by one or more processors (e.g., a processor in control system 112) may cause the one or more processors to perform one or more of the processes 1005-1040. In some embodiments, processes 1025 and 1035 are optional and may be omitted. In some embodiments, method 1000 may include other processes (not shown), such as processes corresponding to one or more of processes 310, 320, 340, 360, and/or 380 of method 300. In some embodiments, method 1000 may be used to deploy various tools, instruments, devices, and/or the like through one or more passageways in order to perform a treatment on target tissue, such as a tumor or lesion in tissue and/or the like.

At a process 1005, a catheter is deployed. In some examples, process 1005 may be substantially the same as process 330, process 405, process 605, and/or process 805.

At a process 1010, a needle/tool is extended to a passageway exit site. In some examples, the needle/tool may be extended though one of the one or more lumens of the catheter until a distal end of the needle reaches the passageway exit site. In some examples, the distal end of the needle/tool may be brought into contact with the passageway wall at the passageway exit site. In some examples, the needle/tool may be extended toward the passageway exit site along an orientation axis consistent with the orientation of the distal end of the catheter.

At a process 1015, the passageway wall at the passageway exit site is penetrated using the needle/tool. In some examples, process 1015 is substantially the same as process 415, process 615, and/or process 815.

At a process 1020, the needle/tool is extended to a target location. In some examples, process 1020 may be substantially the same as process 420, process 620, and/or process 820.

Figure 11:
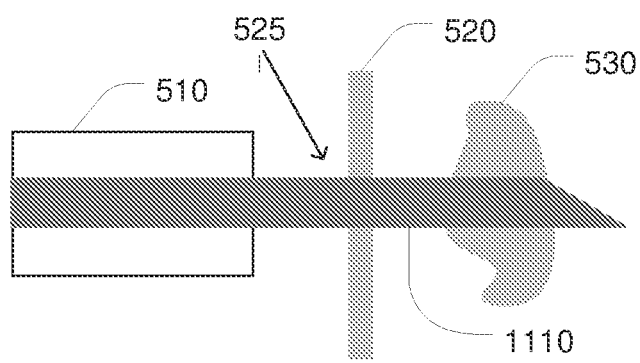
FIG. 11 is a simplified diagram of a device configuration during treatment of tissue according to some embodiments.

FIG. 11 is a simplified diagram of device configuration after the completion of process 1020 according to some embodiments. FIG. 11 shows a needle/tool 1110 extended through passageway wall 520 at passageway exit site 525 and through intervening tissue until needle/tool 1110 is extended through target tissue 530. And although FIG. 11 shows that needle/tool 1110 is extended completely through target tissue 530, in other embodiments, needle/tool 1110 may alternatively be extended to just before target tissue 530 and/or partially through target tissue 530 instead of completely through target tissue 530. And although needle/tool 1110 is shown with a beveled distal end, other shapes for the distal end of needle/tool 1110 are possible, including one or more of a conical distal end, a cross cut distal end, a distal end with one or more crown points, a distal end with one or more bent crown points, and/or the like.

Referring back to FIG. 10, at an optional process 1025, the needle/tool is anchored. In some examples, the needle/tool may be anchored to prevent undesirable movement of the needle/tool during treatment of the tissue. In some examples, the anchoring may include deploying an anchoring device near the distal end of the needle/tool, along a length of the needle/tool, and/or the like. In some examples, the anchoring device may include one or more balloons located at the distal end of the needle/tool and/or along the length of the needle/tool. In some examples, the one or more balloons are inflated by injecting a gas, a fluid, and/or the like through a lumen of the tool. In some examples, the one or more balloons are inflated to anchor corresponding portions of the needle/tool (e.g., the distal end and/or one more locations along the length of the needle/tool and proximal to the distal end) so that the corresponding portions remains effectively stationary during treatment of the target tissue.

At a process 1030, the target tissue is treated. In some examples, process 1030 may be substantially the same as process 455, process 650, and/or process 855.

At an optional process 1035, when the anchoring of the needle/tool occurred during process 1025, the anchoring is removed. In some examples, the anchoring may be removed by evacuating the gas, fluid, and/or the like from the one or more balloons using the lumen within the tool.

At a process 1040, the needle/tool is retracted. In some examples, process 1040 may be substantially the same as process 460, process 660, and/or process 865.

Figure 12:
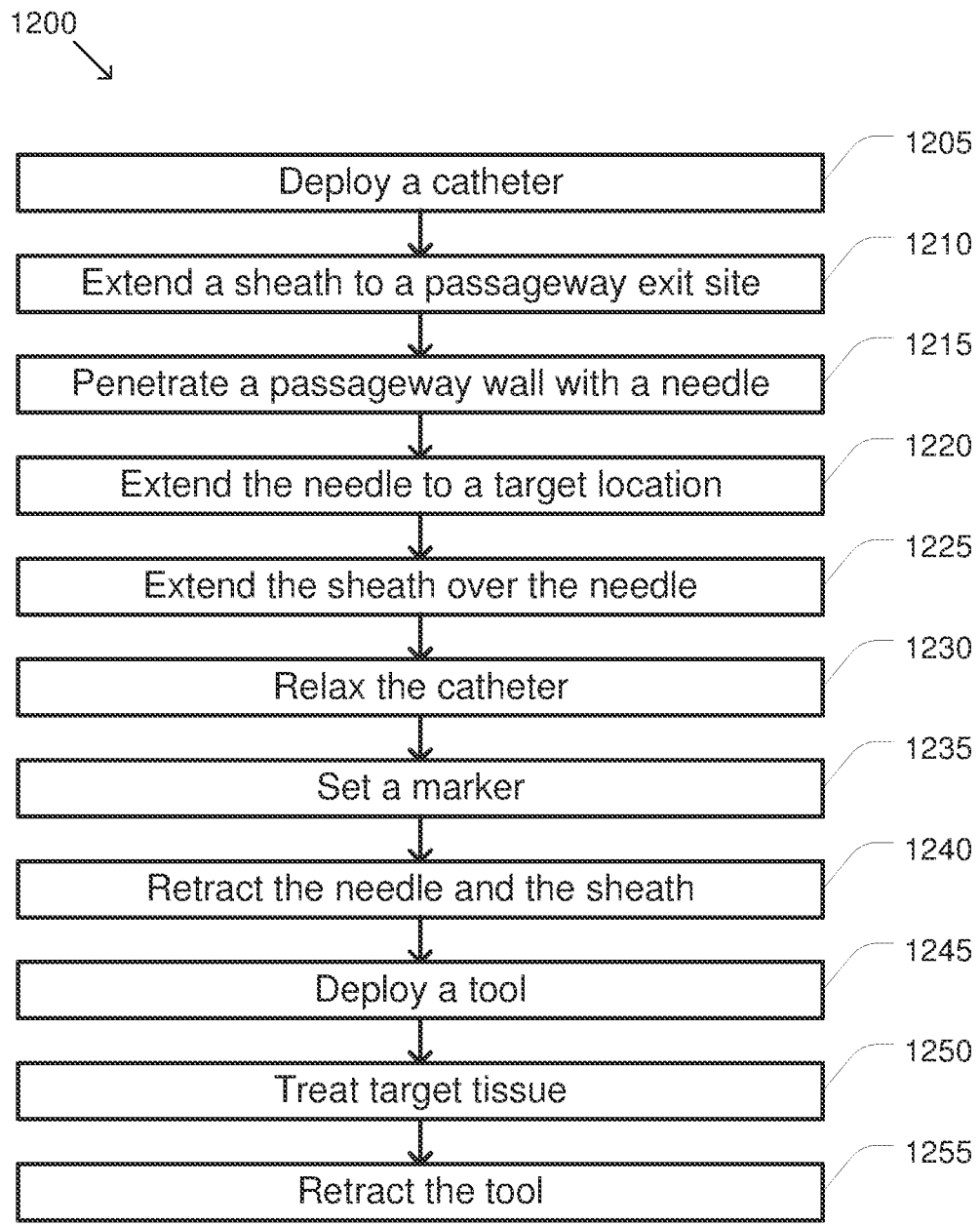
FIG. 12 is a simplified diagram of a method of treating tissue according to some embodiments.

FIG. 12 is a simplified diagram of a method 1200 of treating tissue according to some embodiments. One or more of the processes 1205-1255 of method 1200 may be implemented, at least in part, in the form of executable code stored on non-transitory, tangible, machine-readable media that when run by one or more processors (e.g., a processor in control system 112) may cause the one or more processors to perform one or more of the processes 1205-1255. In some embodiments, process 1235 is optional and may be omitted. In some embodiments, method 1200 may include other processes (not shown), such as processes corresponding to one or more of processes 310, 320, 340, 360, and/or 380 of method 300. In some embodiments, method 1200 may be used to deploy various tools, instruments, devices, and/or the like through one or more passageways in order to perform a treatment on target tissue, such as a tumor or lesion in tissue and/or the like.

At a process 1205, a catheter is deployed. In some examples, process 1205 may be substantially the same as process 330, process 405, process 605, process 805, and/or process 1005.

At a process 1210, the needle is extended to a target location. In some examples, process 820 may be substantially the same as process 420, process 620, and/or process 820.

At a process 1215, the passageway wall at the passageway exit site is penetrated using the needle. In some examples, process 1215 is substantially the same as process 415, process 615, process 815, and/or process 1215.

At a process 1220, the needle is extended to a target location. In some examples, process 1220 may be substantially the same as process 420, process 620, process 820, and/or process 1020.

At a process 1225, the sheath is extended to the target location. In some examples, process 1225 may be substantially the same as process 425 and/or process 625.

At a process 1230, the catheter is relaxed. In some examples, the catheter may be relaxed by reducing a tension in one or more cables, linkages, and/or the like used to steer the catheter during process 12015 (e.g., similar to the one or more cables and/or linkages used to steer elongate device 202). In some examples, relaxing the catheter may allow the catheter to deform with the tissue beyond the passageway wall through which the needle and sheath are extended. In some examples, relaxing the catheter allows the distal end of the catheter to remain in close proximity with and/or aligned with the passageway wall at the passageway exit site even after the needle and catheter are retracted from the tissue during process 1240. In some examples, relaxing the catheter allows a tool to be inserted through the catheter (e.g., during process 1245) without the tool appreciably altering a geometry of the one or more passageways and/or the catheter thus making it more likely that the tool may be passed through the passageway wall at the same passageway exit site as used by the needle and catheter during processes 1220 and 1225, respectively.

At an optional process 1235, a maker is set. In some examples, the marker may set at the passageway exit site to facilitate re-use of the same passageway exit site used by the needle and/or the sheath for a subsequently deployed tool (e.g., during process 1245). In some examples, the marker may be a biopsy marker, a fiducial, a virtual marker, and/or the like.

At a process 1240, the tool and the sheath may be retracted. In some examples, process 1240 may be substantially the same as a combination of process 430, process 630, and/or process 835 along with process 440 and/or process 640.

At a process 1245, a tool is deployed. In some examples, the tool may be deployed by inserting the tool through the lumen of the catheter so that a distal end of the tool reaches the target tissue and/or extends beyond the target tissue. In some examples, the tool may be deployed through the same passageway exit site used by the needle and the sheath. In some examples, the marker set during optional process 1235 may be used to help facilitate using the same passageway exit site. In some examples, the distal end of the catheter may be steered (e.g., using a process similar to process 605) to help align the tool with the same passageway exit site.

At a process 1250, the target tissue is treated. In some examples, process 1250 may be substantially the same as process 455, process 650, process 855, and/or process 1030.

At a process 1255, the needle/tool is retracted. In some examples, process 1255 may be substantially the same as process 460, process 660, process 865, and/or process 1040.

As discussed above and further emphasized here, FIGS. 3-12 are merely examples which should not unduly limit the scope of the claims. One of ordinary skill in the art would recognize many variations, alternatives, and modifications. According to some embodiments, methods 300, 400, 600, 800, and/or 1000 may be repeated multiple times to treat multiple target tissue sites and/or target tissue sites that are too large and/or are shaped so that treatment from one target location is not practical. In some examples, the set-up and planning of process 310 may be adapted to select multiple target treatment sites that are able to treat all of the target tissue while minimizing overlap of treatment of portions of the target tissue from two or more target treatment sites.

In some examples, methods 300, 400, 600, 800, and/or 1000 may be repeated by positioning the one or more tools/instruments/devices at a first position and orientation relative to the target tissue, confirming the positioning and/or orientation, repositioning and/or reorienting the one or more tools/instruments/devices, performing a treatment, and confirming successful treatment before repeating the process to reposition the one or more tools/instruments/devices to treat another portion of the target tissue and/or another target tissue. In some examples, the repositioning and/or reorienting may include one or more of repositioning and/or reorienting the catheter using processes 320, 405, 605, 805, and/or 1005, extending and/or reorienting the needle using processes 350, 420, 620, 820, and/or 1020, redeploying the guide wire using process 435, deploying the tool to a different position along the guide wire using process 450, anchoring the guide wire and/or the tool at a different location using processes 440, 645, 850, and/or 1025, redeploying the tool using process 350, 450, 635, 840, 1020, and/or the like. In some examples, methods 300, 400, 600, 800, and/or 1000 may further include one or more processes to confirm whether additional treatment is to be performed and one or more of the processes of methods 300, 400, 600, 800, and/or 1000 are to be repeated.

In some embodiment, each repetition of methods 300, 400, 600, 800, and/or 1000 may include switching between methods 300, 400, 600, 800, and/or 1000 as different tools/instruments/devices and/or treatment modalities are to be used.

In some embodiments, after confirmation of a location of the target tissue and/or confirmation of successful treatment of the tissue, pre-operative models such as models generated during process 310, may be altered or updated to reflect a shift in position of the target tissue, to reflect complete treatment, to add an indicator of treated area, and/or the like. Some examples of working with elongate devices and image models are described further in commonly-owned International Patent Application No. PCT/US201812969 (filed Jan. 9, 2018) (disclosing "Systems and Methods for Registering Elongate Devices to Three Dimensional Images in Image-Guided Procedures"), which is incorporated by reference herein in its entirety.

In some embodiments, methods 300, 400, 600, 800, and/or 1000 may include additional processes that are not shown. In some examples, the needle may be used to take a sample or perform a biopsy before it is retracted and/or before the tissue is treated. In some examples, the needle may be used to inject a thermal accelerant and/or other chemical (e.g., a therapeutic drug) before the needle is retracted and/or before the tissue is treated.

One or more elements in embodiments of the invention (e.g., the processing of signals received from the input controls and/or control of the elongate device) may be implemented in software to execute on a processor of a computer system, such as control system 112. When implemented in software, the elements of the embodiments of the invention are essentially the code segments to perform the necessary tasks. The program or code segments can be stored in a non-transitory machine-readable storage media, including any media that can store information including an optical medium, semiconductor medium, and magnetic medium. Machine-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

ADDITIONAL EXAMPLES

1. A method of treating target tissue located among one or more passageways, the method comprising:
deploying a distal end of a flexible elongate device having a lumen along the one or more passageways near a passageway exit site;
extending a hollow sheath within the lumen and past the distal end of the flexible elongate device to the passageway exit site;
extending a needle within the hollow sheath and to a target location associated with the target tissue;
extending the hollow sheath along the needle;
retracting the needle from the hollow sheath;
deploying a tool to the target location; and
performing treatment on the target tissue around the target location using the tool.

2. The method of example 1, further comprising retracting the hollow sheath before performing the treatment on the target tissue.

3. The method of example 1, further comprising aligning the distal end of the flexible elongate device toward the target tissue.

4. The method of example 1, further comprising adjusting an angle of the hollow sheath toward the passageway exit site.

5. The method of example 1, further comprising confirming a location of the distal end of the flexible elongate device before extending the hollow sheath to the passageway exit site.

6. The method of example 1, further comprising confirming a location of the tool before performing the treatment on the target tissue.

7. The method of example 1, further comprising confirming treatment of the target tissue.

8. The method of example 1, further comprising taking a sample using the needle before retracting the needle.

9. The method of example 1, further comprising delivering a chemical using the needle before retracting the needle.

10. The method of example 9, wherein the chemical is a therapeutic drug, a radioactive tissue, or an accelerant.

11. The method of example 1, further comprising:
deploying a guide wire within the hollow sheath; and
deploying the tool over the guide wire.

12. The method of example 11, further comprising anchoring a distal end of the guide wire.

13. The method of example 12, wherein anchoring the distal end of the guide wire comprises inflating one or more balloons.

14. The method of example 1, further comprising anchoring the tool.

15. The method of example 14, wherein anchoring the tool comprises at least one of anchoring a distal end of the tool, anchoring the tool along a length of the tool, or inflating one or more balloons.

16. The method of example 14, wherein anchoring the tool comprises deploying one or more barbs.

17. The method of example 16, further comprising re-extending the hollow sheath over the tool to collapse the one or more barbs.

18. The method of any one of examples 1 or 2-17, wherein the target tissue is one of at least anatomical tissue, a lesion, a nodule, or a tumor.

19. The method of any one of examples 1 or 2-17, wherein the tool is a sampling tool, a chemical deployment tool, an ablation tool, an imaging tool, or a sensing tool.

20. The method of any one of examples 1 or 2-17, wherein the treatment comprises RF ablation or microwave ablation.

21. A method of treating target tissue located among one or more passageways, the method comprising:
deploying a distal end of a flexible elongate device having a lumen along the one or more passageways near a passageway exit site;
extending a first hollow sheath within the lumen and past the distal end of the flexible elongate device to the passageway exit site;
extending a needle within the first hollow sheath and to a target location associated with the target tissue;
retracting the first hollow sheath;
extending a second hollow sheath along the needle;
retracting the needle from the second hollow sheath;
deploying a tool to the target location; and
performing treatment on the target tissue around the target location using the tool.

22. The method of example 21, further comprising retracting the second hollow sheath before performing the treatment on the target tissue.

23. The method of example 21, further comprising confirming a location of the distal end of the flexible elongate device before extending the first hollow sheath to the passageway exit site.

24. The method of example 21, further comprising confirming a location of the tool before performing the treatment on the target tissue.

25. The method of example 21, further comprising confirming treatment of the target tissue.

26. The method of example 21, further comprising anchoring the tool.

27. The method of example 26, wherein anchoring the tool comprises at least one of anchoring a distal end of the tool, anchoring the tool along a length of the tool, or inflating one or more balloons.

28. The method of example 26, wherein anchoring the tool comprises deploying one or more barbs.

29. The method of example 28, further comprising re-extending the hollow sheath over the tool to collapse the one or more barbs.

30. The method of any one of examples 21 or 22-29, wherein an inner diameter of the first hollow sheath is smaller than an inner diameter of the second hollow sheath.

31. The method any one of examples 21 or 22-29, wherein the target tissue is one of at least anatomical tissue, a lesion, a nodule, and a tumor.

32. The method of any one of examples 21 or 22-29, wherein the tool is a sampling tool, a chemical deployment tool, an ablation tool, an imaging tool, or a sensing tool.

33. The method of any one of examples 21 or 22-29, wherein the treatment comprises RF ablation or microwave ablation.

34. A method of treating target tissue located among one or more passageways, the method comprising:
deploying a distal end of a flexible elongate device having a lumen along the one or more passageways near a passageway exit site;
extending a tool within the lumen and past the distal end of the flexible elongate device to the passageway exit site and to a target location associated with the target tissue;
anchoring the tool;
performing treatment on the target tissue around the target location using the tool;

removing the anchoring; and
retracting the tool.

35. The method of example 34, further comprising confirming a location of the distal end of the flexible elongate device before extending the tool to the target location.

36. The method of example 34, further comprising confirming a location of the tool before performing the treatment on the target tissue.

37. The method of example 34, further comprising confirming treatment of the target tissue.

38. The method of example 34, wherein anchoring the tool comprises at least one of anchoring a distal end of the tool, anchoring the tool along a length of the tool, or inflating one or more balloons.

39. The method of example 34, wherein anchoring the tool comprises deploying one or more barbs.

40. The method of example 39, further comprising re-extending the hollow sheath over the tool to collapse the one or more barbs.

41. The method any one of examples 34 or 35-40, wherein the target tissue is one of at least anatomical tissue, a lesion, a nodule, or a tumor.

42. The method of any one of examples 34 or 35-40, wherein the tool is a sampling tool, a chemical deployment tool, an ablation tool, an imaging tool, or a sensing tool.

43. The method of any one of examples 34 or 35-40, wherein the treatment comprises RF ablation or microwave ablation.

44. A method of treating target tissue located among one or more passageways, the method comprising:
   deploying a distal end of a flexible elongate device having a lumen along the one or more passageways near a passageway exit site;
   extending a hollow sheath within the lumen and past the distal end of the flexible elongate device to the passageway exit site;
   extending a needle within the hollow sheath and to a target location associated with the target tissue;
   extending the hollow sheath along the needle;
   relaxing at least the distal end of the flexible elongate device;
   retracting the needle and the sheath;
   deploying a tool to the target location; and
   performing treatment on the target tissue around the target location using the tool.

45. The method of example 44, further comprising deploying the tool to the target location through the passageway exit site.

46. The method of example 44, further comprising marking the passageway exit site with a marker.

47. The method any one of examples 44 or 45-46, wherein the target tissue is one of at least anatomical tissue, a lesion, a nodule, or a tumor.

48. The method of any one of examples 44 or 45-46, wherein the tool is a sampling tool, a chemical deployment tool, an ablation tool, an imaging tool, or a sensing tool.

49. The method of any one of examples 44 or 45-46, wherein the treatment comprises RF ablation or microwave ablation.

What is claimed is:

1. A method comprising:
   deploying a tool to a passageway exit site through a lumen of a flexible elongate device comprising a proximal end, a distal end, and the lumen therebetween, the tool comprising a needle, a first hollow sheath, and a second hollow sheath, wherein deploying the tool to the passageway exit site includes deploying the first hollow sheath past the distal end of the flexible elongate device to the passageway exit site;
   puncturing a passageway wall at the passageway exit site with the needle;
   deploying the needle through the passageway wall and through target tissue at a target location beyond the passageway wall;
   retracting the first hollow sheath, after being deployed to the passageway exit site, and removing the first hollow sheath from the lumen of the flexible elongate device;
   deploying the second hollow sheath within the lumen of the flexible elongate device and extending the second hollow sheath along the needle to the target location;
   retracting the needle, after the second hollow sheath is at the target location, from the second hollow sheath;
   deploying an instrument, after the needle is retracted from the second hollow sheath, to perform treatment on the target tissue at the target location, the instrument deployed through a second lumen of the second hollow sheath and through a perforation created in the target tissue by the needle; and
   anchoring the tool by an anchor of a guidewire before performing treatment on the target tissue.

2. The method of claim 1, wherein a distal end of the needle comprises one or more of a beveled end, a conical end, a cross-cut end, a crown point, or a bent crown point.

3. A method, comprising:
   deploying a tool to a passageway exit site through a lumen of a flexible elongate device comprising a proximal end, a distal end, and the lumen therebetween, the tool comprising a needle and a hollow sheath, wherein deploying the tool to the passageway exit site comprises deploying the hollow sheath past the distal end of the flexible elongate device to the passageway exit site;
   puncturing a passageway wall at the passageway exit site with the needle;
   deploying the needle through the passageway wall and through target tissue at a target location beyond the passageway wall;
   extending the hollow sheath along the needle;
   retracting the needle from the hollow sheath;
   deploying an instrument to perform treatment on the target tissue at the target location, the instrument deployed within the tool and through a perforation created in the target tissue by the needle;
   retracting the hollow sheath, after extending the first hollow sheath along the needle;
   removing the hollow sheath from the target tissue; and
   positioning the hollow sheath at the passageway exit site.

4. The method of claim 3, further comprising inserting a portion of a guidewire including an anchor through the target tissue within the perforation.

5. The method of claim 4, further comprising:
   deploying the guidewire through the hollow sheath after the needle is retracted from the hollow sheath; and
   anchoring the guidewire proximate the target tissue.

6. The method of claim 5, wherein
   positioning the hollow sheath at the passageway exit site occurs after the guidewire is anchored proximate the target tissue.

7. The method of claim 4, wherein the anchor includes one or more balloons, one or more barbs, one or more teeth, one or more tines, or one or more cleats.

8. The method of claim 3, further comprising extending the hollow sheath through the target tissue to position a portion of a guidewire including an anchor at least partially within the target tissue.

9. A method, comprising:

deploying a tool to a passageway exit site through a lumen of a flexible elongate device comprising a proximal end, a distal end, and the lumen therebetween, the tool comprising a needle and a hollow sheath;

puncturing a passageway wall at the passageway exit site with the needle;

deploying the needle through the passageway wall and through target tissue at a target location beyond the passageway wall;

extending the hollow sheath through the target tissue;

inserting a portion of a guidewire including an anchor through a perforation created in the target tissue by the needle including deploying the guidewire through the hollow sheath after the needle is retracted from the hollow sheath and anchoring the guidewire proximate the target tissue;

retracting the hollow sheath from the target tissue;

positioning the hollow sheath at the passageway exit site, after the guidewire is anchored proximate the target tissue; and deploying an instrument along the guidewire when the guidewire is anchored proximate the target tissue to perform treatment on the target tissue at the target location, the instrument deployed within the hollow sheath and through the perforation.

10. The method of claim 9, wherein the flexible elongate device further comprises a shape sensor.

11. The method of claim 10, further comprising confirming, with a control unit coupled to the instrument and based on data from the shape sensor, a location of the distal end of the flexible elongate device before deploying the hollow sheath to the passageway exit site.

12. The method of claim 11, further comprising confirming, with the control unit, a location of the distal end of the flexible elongate device before deploying the instrument to the target location.

13. The method of claim 11, further comprising confirming, with the control unit, a location of the instrument before performing the treatment on the target tissue.

14. The method of claim 10, further comprising measuring, with a sensor system, data for confirming treatment of the target tissue, wherein the sensor system measures at least one of temperature or impedance of the target tissue.

* * * * *